US008142189B2

(12) United States Patent
Brajnovic

(10) Patent No.: US 8,142,189 B2
(45) Date of Patent: Mar. 27, 2012

(54) ARRANGEMENT AND DEVICE FOR USING A TEMPLATE TO FORM HOLES FOR IMPLANTS IN BONE, PREFERABLY JAW BONE

(75) Inventor: Izidor Brajnovic, Rydal (SE)

(73) Assignee: Noble Biocare Services AG (CH)

(*) Notice: Subject to any disclaimer, the term of this patent is extended or adjusted under 35 U.S.C. 154(b) by 35 days.

(21) Appl. No.: 12/548,328

(22) Filed: Aug. 26, 2009

(65) Prior Publication Data

US 2010/0075275 A1  Mar. 25, 2010

Related U.S. Application Data

(63) Continuation of application No. 10/710,170, filed on Jun. 23, 2004, now Pat. No. 7,950,924, which is a continuation of application No. PCT/SE02/02393, filed on Dec. 19, 2002.

(30) Foreign Application Priority Data

Dec. 28, 2001 (SE) ...................................... 0104431

(51) Int. Cl.
*A61C 3/00* (2006.01)
(52) U.S. Cl. ......................................................... 433/75
(58) Field of Classification Search .................... 433/75, 433/72, 76, 172–176; 33/513, 514; 606/96–98; 700/98, 118; 703/1
See application file for complete search history.

(56) References Cited

U.S. PATENT DOCUMENTS 3,436,826 A    4/1969 Edelman
4,315,740 A    2/1982 Mercer et al.
4,470,815 A    9/1984 Hazar
4,832,601 A    5/1989 Linden
(Continued)

FOREIGN PATENT DOCUMENTS

DE    94 20 038    3/1995
(Continued)

OTHER PUBLICATIONS

International Search Report for Application No. PCT/SE 2003/001976 (the PCT counterpart of abandoned U.S. Appl. No. 11/172,354 and co-pending U.S. Appl. No. 12/014,031) mailed Mar. 11, 2004 in 2 pages.
(Continued)

*Primary Examiner* — Sunil K Singh
(74) *Attorney, Agent, or Firm* — Knobbe Martens Olson & Bear, LLP

(57) ABSTRACT

An apparatus includes a template which locates hole positions in a jawbone while the template is separated from the jawbone by gum tissue. The template follows a contour of the gum tissue surrounding the jawbone and has guide holes which receive a cutting tool. Anchoring elements attach the template to the jawbone. A system includes means for scanning an implantation site on a patient's jawbone, simulating the implantation site, and determining nerve-rich areas or nerve paths in the jawbone. A holed template is produced which is separated from the jawbone by at least gum tissue of the patient. Attachment hole positions in the jawbone are located so as to avoid nerve paths. A method of forming holes to attach a dental implant to a patient's jaw bone without surgical intervention in gum tissue of the patient to expose the jawbone is disclosed which avoids impingement on a nerve path.

10 Claims, 3 Drawing Sheets

U.S. PATENT DOCUMENTS

| | | | |
|---|---|---|---|
| 4,850,870 A | 7/1989 | Lazzara et al. |
| 4,906,420 A | 3/1990 | Brajnovic et al. |
| 4,998,881 A | 3/1991 | Lauks |
| 5,015,183 A | 5/1991 | Fenick |
| 5,030,096 A | 7/1991 | Hurson et al. |
| 5,062,800 A | 11/1991 | Niznick |
| 5,106,300 A | 4/1992 | Voitik |
| 5,213,502 A | 5/1993 | Daftary |
| 5,320,529 A | 6/1994 | Pompa |
| 5,350,297 A | 9/1994 | Cohen |
| 5,482,463 A | 1/1996 | Wilson et al. |
| 5,538,426 A | 7/1996 | Harding et al. |
| 5,554,027 A | 9/1996 | Branemark |
| 5,577,912 A | 11/1996 | Prins |
| 5,605,457 A | 2/1997 | Bailey et al. |
| 5,605,458 A | 2/1997 | Bailey et al. |
| 5,607,304 A | 3/1997 | Bailey et al. |
| 5,613,852 A | 3/1997 | Bavitz |
| 5,636,989 A | 6/1997 | Somborac et al. |
| 5,651,675 A | 7/1997 | Singer |
| 5,662,473 A | 9/1997 | Rassoli et al. |
| 5,681,167 A | 10/1997 | Lazarof |
| 5,718,579 A | 2/1998 | Kennedy |
| 5,725,376 A | 3/1998 | Poirier |
| 5,743,916 A | 4/1998 | Greenberg et al. |
| 5,768,134 A | 6/1998 | Swaelens et al. |
| 5,788,494 A | 8/1998 | Phimmasone |
| 5,823,776 A | 10/1998 | Duerr et al. |
| 5,851,115 A | 12/1998 | Carlsson et al. |
| 5,876,204 A | 3/1999 | Day et al. |
| 5,938,686 A | 8/1999 | Benderev et al. |
| 5,939,211 A | 8/1999 | Mörmann |
| 5,967,305 A | 10/1999 | Blonder et al. |
| 5,989,028 A | 11/1999 | Niznick |
| 6,099,311 A | 8/2000 | Wagner et al. |
| 6,159,008 A | 12/2000 | Kumar |
| 6,174,166 B1 | 1/2001 | Jörneus |
| 6,217,332 B1 | 4/2001 | Kumar |
| 6,227,861 B1 | 5/2001 | Cartledge et al. |
| 6,254,639 B1 | 7/2001 | Peckitt |
| 6,280,194 B1 | 8/2001 | Björn et al. |
| 6,287,117 B1 | 9/2001 | Niznick |
| 6,287,119 B1 | 9/2001 | Van Nifterick et al. |
| 6,305,939 B1 | 10/2001 | Dawood |
| 6,312,260 B1 | 11/2001 | Kumar et al. |
| 6,315,562 B1 | 11/2001 | Kumar |
| 6,319,000 B1 | 11/2001 | Branemark |
| 6,375,465 B1 | 4/2002 | Engman et al. |
| 6,382,975 B1 * | 5/2002 | Poirier ............................ 433/173 |
| 6,488,502 B1 | 12/2002 | Weber |
| 6,561,805 B2 | 5/2003 | Kumar |
| 6,619,958 B2 | 9/2003 | Beaty et al. |
| 6,626,911 B1 | 9/2003 | Engman et al. |
| 6,627,327 B2 | 9/2003 | Reidt et al. |
| 6,640,150 B1 | 10/2003 | Perrson |
| 6,660,400 B1 | 12/2003 | Hintersehr |
| 6,672,870 B2 * | 1/2004 | Knapp .............................. 433/76 |
| 6,692,254 B1 | 2/2004 | Kligerman et al. |
| 6,705,863 B2 | 3/2004 | Phan et al. |
| 6,793,491 B2 | 9/2004 | Klein et al. |
| 6,814,575 B2 | 11/2004 | Poirier et al. |
| 6,824,384 B1 | 11/2004 | Bompard et al. |
| 6,827,575 B1 | 12/2004 | Jörneus |
| 6,857,874 B2 | 2/2005 | Kim |
| 6,997,707 B2 | 2/2006 | Germanier |
| 7,021,934 B2 | 4/2006 | Aravena |
| 7,027,642 B2 | 4/2006 | Rubbert et al. |
| 7,175,435 B2 | 2/2007 | Andersson et al. |
| 7,331,786 B2 | 2/2008 | Poirier |
| 7,338,286 B2 | 3/2008 | Porter et al. |
| 2002/0102517 A1 | 8/2002 | Poirier |
| 2002/0106604 A1 | 8/2002 | Phan et al. |
| 2002/0177104 A1 | 11/2002 | Klein et al. |
| 2003/0186187 A1 | 10/2003 | Germanier |
| 2004/0015327 A1 | 1/2004 | Sachdeva et al. |
| 2004/0259051 A1 | 12/2004 | Brajnovic et al. |
| 2005/0170311 A1 | 8/2005 | Tardieu et al. |
| 2006/0008763 A1 | 1/2006 | Brajnovic et al. |
| 2006/0008770 A1 | 1/2006 | Brajnovic et al. |
| 2006/0240378 A1 | 10/2006 | Weinstein et al. |
| 2007/0281270 A1 | 12/2007 | Brajnovic |
| 2008/0038692 A1 | 2/2008 | Andersson et al. |
| 2008/0118895 A1 | 5/2008 | Brajnovic |
| 2008/0153065 A1 | 6/2008 | Brajnovic et al. |
| 2008/0220390 A1 | 9/2008 | Klien |

FOREIGN PATENT DOCUMENTS

| | | |
|---|---|---|
| DE | 100 09 448 | 9/2001 |
| DE | 601 26 120 | 11/2007 |
| EP | 0689804 A1 | 1/1996 |
| EP | 1205159 | 5/2002 |
| EP | 1317910 A1 | 6/2003 |
| EP | 1364625 A1 | 11/2003 |
| FR | 2836372 A1 | 8/2003 |
| GB | 1131948 | 10/1968 |
| JP | 2004 521671 | 7/2004 |
| SE | 457691 | 1/1989 |
| SE | 508662 | 10/1998 |
| SE | 522958 C2 | 3/2004 |
| WO | WO 94/14388 A1 | 7/1994 |
| WO | WO 96/37163 A1 | 11/1996 |
| WO | WO 97/49351 | 12/1997 |
| WO | WO 98/16163 | 4/1998 |
| WO | WO 98/44865 A1 | 10/1998 |
| WO | WO 99/26540 | 6/1999 |
| WO | WO 00/27300 | 5/2000 |
| WO | WO 00/28914 | 5/2000 |
| WO | WO 01/54609 | 8/2001 |
| WO | WO 01/58379 A1 | 8/2001 |
| WO | WO 02/38074 | 5/2002 |
| WO | WO 02/053055 A1 | 7/2002 |
| WO | WO 02/053056 A1 | 7/2002 |
| WO | WO 02/053057 A1 | 7/2002 |
| WO | WO 2004/098378 A3 | 11/2004 |
| WO | WO 2006/082198 | 1/2006 |
| WO | WO 2007/129955 | 11/2007 |

OTHER PUBLICATIONS

International Search Report for Application No. PCT/SE 2002/02393 (the PCT counterpart of co-pending U.S. Appl. No. 10/710,170) mailed Mar. 20, 2003 in 2 pages.

International Preliminary Report on Patentability for Application No. PCT/SE 2002/02393 (the PCT counterpart of co-pending U.S. Appl. No. 10/710,170) completed on Mar. 8, 2004 in 3 pages.

International Search Report for Application No. PCT/SE 2003/001975 (the PCT counterpart of U.S. Appl. No. 11/172,291) completed on Feb. 2, 2005 in 4 pages.

International Preliminary Report on Patentability and Written Opinion for Application No. PCT/SE 2003/001975 (the PCT counterpart of U.S. Appl. No. 11/172,291) mailed on Feb. 2, 2005 in 4 pages.

International Search Report for Application No. PCT/SE 2004/001527 (the PCT counterpart of co-pending U.S. Appl. No. 10/582,417) mailed Jan. 21, 2005 in 3 pages.

International Preliminary Report on Patentability and Written Opinion for Application No. PCT/SE 2004/001527 (the PCT counterpart of co-pending U.S. Appl. No. 10/582,417) mailed on Jan. 21, 2005 in 7 pages.

International Search Report for Application No. PCT/SE 2005/001074 (the PCT counterpart of co-pending U.S. Appl. No. 11/573,193 mailed Nov. 2, 2005 in 3 pages.

International Preliminary Report on Patentability and Written Opinion for Application No. PCT/SE 2005/001074 (the PCT counterpart of co-pending U.S. Appl. No. 11/573,193 mailed Nov. 2, 2005 in 7 pages.

International Search Report for Application No. PCT/SE 2005/001075 (the counterpart of the co-pending U.S. Appl. No. 11/573,196).

International Preliminary Report on Patentability and Written Opinion for Application No. PCT/SE 2005/001075 (the counterpart of the co-pending U.S. Appl. No. 11/573,196) mailed Nov. 2, 2005 in 7 pages.

International Search Report for Application No. PCT/SE 2007/000431 (the counterpart of U.S. Appl. No. 12/299,598) mailed Apr. 9, 2007 in 4 pages.

International Preliminary Report on Patentability and Written Opinion for Application No. PCT/SE 2007/000431 (the counterpart of U.S. Appl. No. 12/299,598) mailed on Apr. 9, 2007 in 13 pages.

International Search Report for Application No. PCT/SE 2001/002898 (the counterpart of the U.S. Appl. No. 10/451,535 mailed Nov. 4, 2002 in 4 pages.

International Preliminary Report on Patentability and Written Opinion for Application No. PCT/SE 2001/002898 (the counterpart of U.S. Appl. No. 10/451,535 completed on Dec. 9, 2002 in 5 pages.

Tardieu P.B. and B. Philippe: 'Total maxillary edentation with terminal osseus atrophy therapeutic treatment' Implant vol. 7, No. 3, 2000, pp. 199-210.

Tardieu P.: 'Computer assistance in the planning and implementation of implant treatments. The Materialise concept and the SurgiCase Programme.' WWW.DENTALESPACE.COM 2000, pp. 1-11.

European Patent Office Communication Pursuant to Rule 114(2) EPC with Third Party Observation Letter mailed Mar. 6, 2009 in 4 pages, received in corresponding EP Application No. 02793696.2 (EP counterpart of 290C1).

Tardieu, Philippe B. : "Aide Informatique Aux Diagnostics Et Aux Traitement Implantaires. Guides Chirurgico-Scannographiques. Programme Simm:Plan." Believed to be published in 1999. pp. 1-27.

International Search Report for Application No. PCT/EP2007/050426 (the PCT counterpart of co-pending U.S. Appl. No. 12/522,706) mailed Oct. 16, 2007 in 3 pages.

Gateno et al., A New Technique for the Creation of a Computerized Composite Skull Model, J Oral Maxillofac Surg, 2003, vol. 61, pp. 222-227.

* cited by examiner

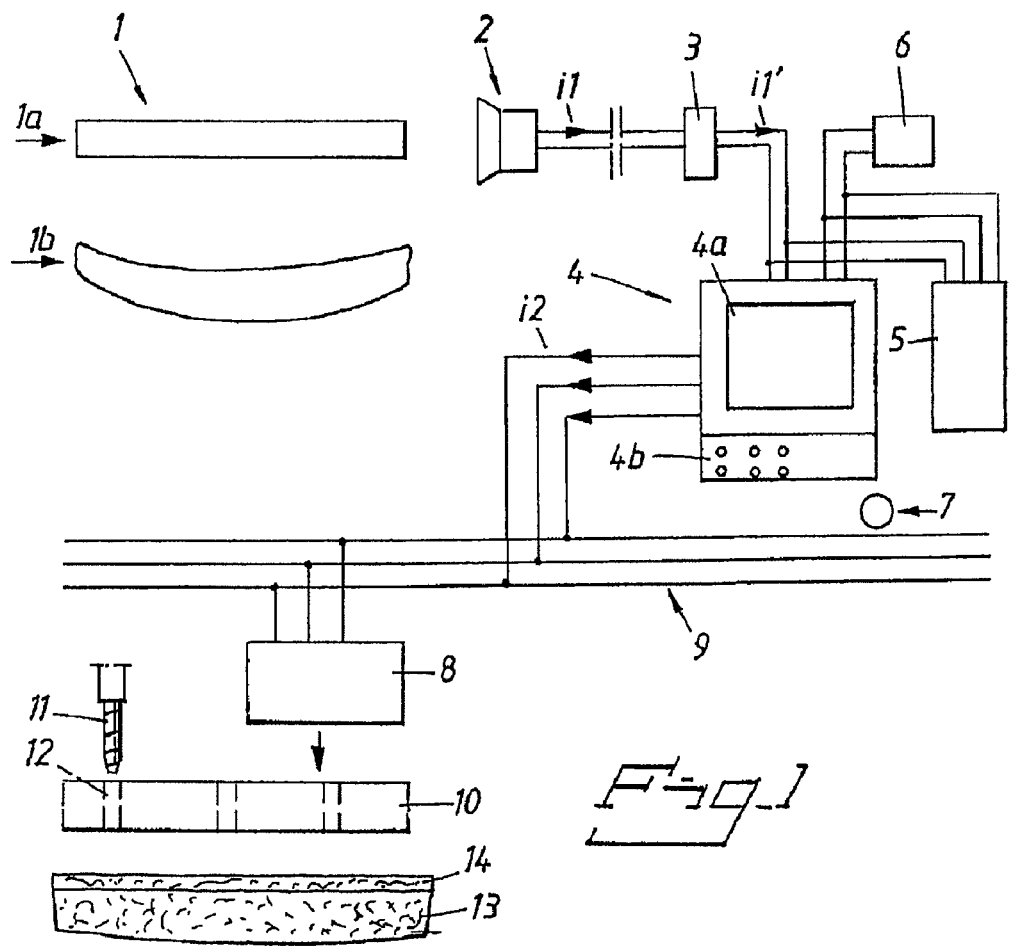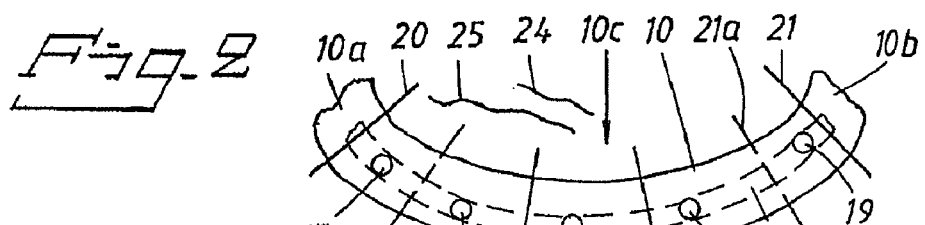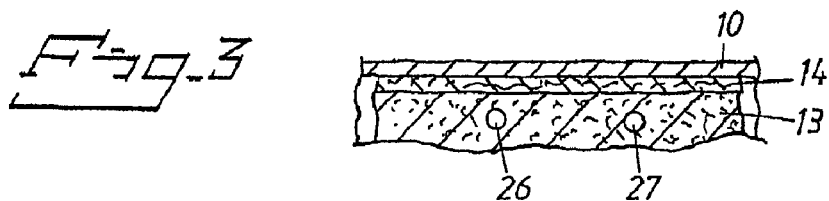

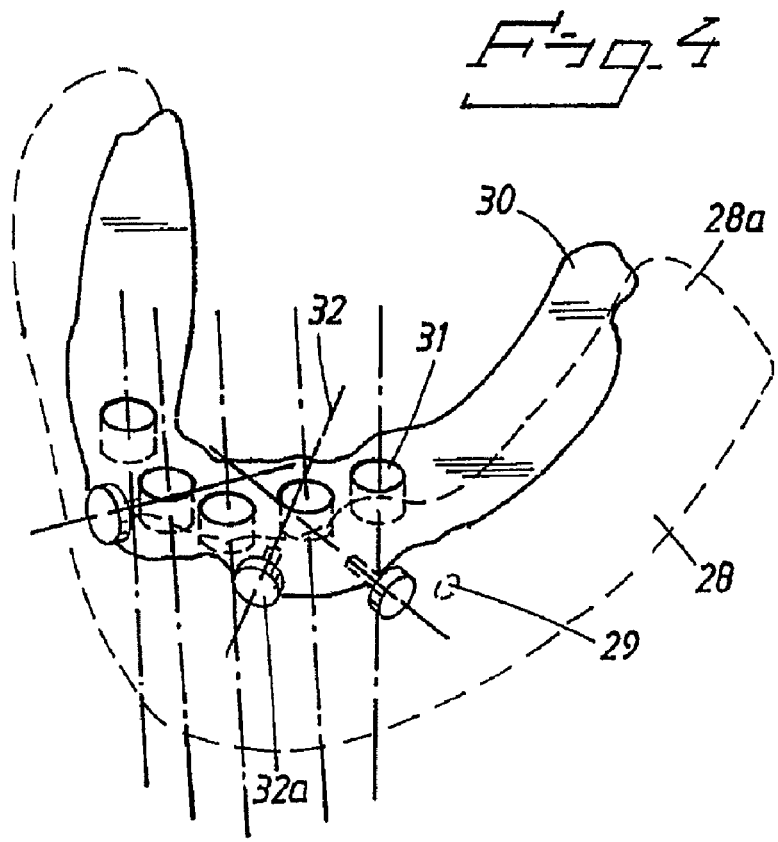
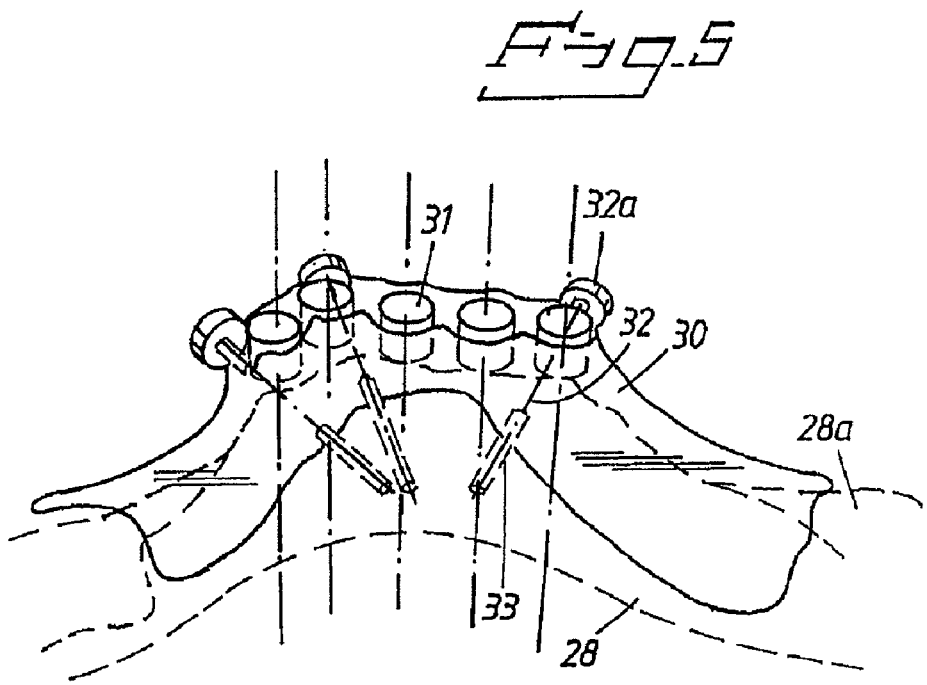

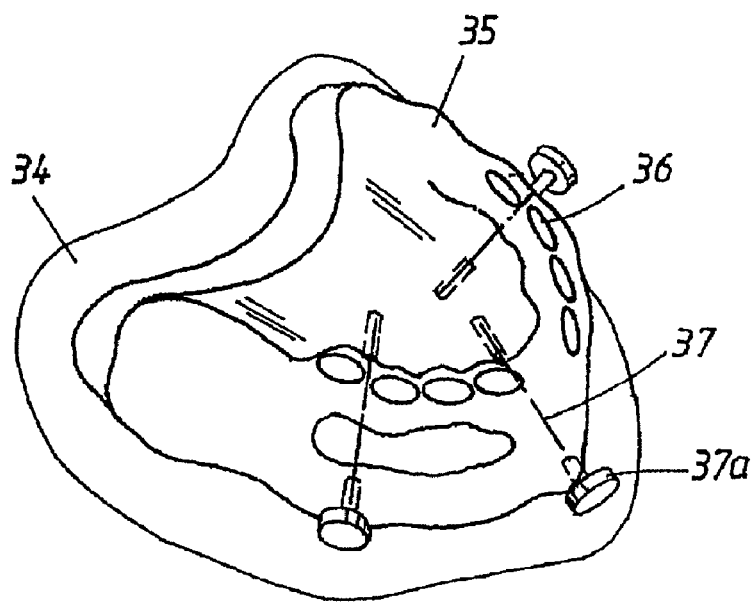
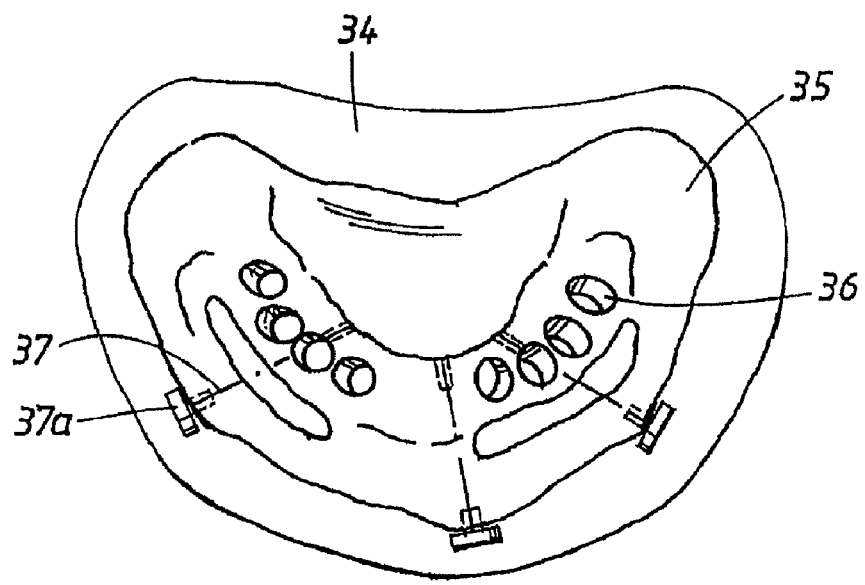

ARRANGEMENT AND DEVICE FOR USING A TEMPLATE TO FORM HOLES FOR IMPLANTS IN BONE, PREFERABLY JAW BONE

CROSS-REFERENCE TO RELATED APPLICATIONS

This Application is a continuation of U.S. patent application Ser. No. 10/710,170, now issued as U.S. Pat. No. 7,950,924, filed Jun. 23, 2004, which is a continuation of International Application No. PCT/SE02/02393, with an international filing date of Dec. 19, 2002, which claims priority under 35 U.S.C. §119 to Swedish Patent Application No. SE 0104431-2, filed on Dec. 28, 2001 in Sweden. The entire contents of each of the foregoing applications are incorporated herein by reference.

BACKGROUND OF THE INVENTION

This disclosure relates in various aspects to an arrangement for using a template to form holes for implants in bone, preferably jaw bone, without any negative effect from the existing resiliency in the flesh surrounding the bone, for example the gum (gingiva). The template in question may be adapted to the shape or shapes of the bone and of the gum and has guide holes for a hole-forming unit which can consist of conventional drill equipment.

This disclosure also relates to a device in accordance with the above in which a holed template is arranged to be applied to an implantation site. The device in this case comprises one or more first apparatus arranged to scan the implantation site and initiate electronic, preferably digital, signals concerning the implantation site and send them to a computer processor. The processor may be arranged and operated to simulate the implantation site and the holed template which is adapted to the implantation site. The processor may be arranged to supply information on all or part of the simulated situation, and may also be arranged to forward or transmit the information to a second apparatus designed to cooperate with production equipment relating to the simulated holed template.

It has long been known to use templates to form holes in the jaw bone, for example. It is also known that it can be difficult to obtain the necessarily exact hole formation unless the gum, i.e. the gingiva, is folded back and the jaw bone thereby exposed, because the gum resilient properties can interfere with the template application and the hole formation.

There is a great disadvantage in carrying out surgical interventions for exposing the jaw bone, i.e. by folding back the gum. This causes inconveniences for the patient, and the implantation work is also painful because the formation of the hole and insertion of the implant have to be followed by a process of healing, which can last some considerable time.

What is needed then is an apparatus, system, and method to substantially shorten the time required for the implantation work. What is further needed is a system and method which uses computer-based scanning and production for the templates and the implantation process.

SUMMARY OF THE INVENTION

In one embodiment, an arrangement includes a template designed for application to the bone (the jaw bone) with the gum (gingiva) lying in between, wherein the template is arranged with two or more anchoring elements intended to extend through the gum and into and preferably through substantial parts of the whole bone, the hole forming unit being arranged to penetrate through the gum during hole formation in the bone (jaw bone).

In further aspects of this embodiment, the template is arranged to form holes for implants for anchoring a dental bridge with several implant attachments. The anchoring elements can have long and narrow or needle-shaped designs, and can be arranged to extend through side holes or side recesses in the side walls of the template. The anchoring elements for dental bridges are at least three in number, two of the anchoring elements being arranged on or at a distance from the ends of the bridge, and one or more anchoring elements are arranged at the central parts of the dental bridge. Each anchoring element may be arranged to extend substantially horizontally through the gum and the jaw bone. Alternatively, or in addition to this, the anchoring elements can extend only partially into the gum.

In an aspect of this embodiment, an apparatus useful in a dental implant procedure includes a template suitable for locating hole positions in a patient's jawbone with the template separated from the jawbone by at least gum tissue of the patient. The template may be shaped to follow a contour of the gum tissue surrounding the jawbone and having guide holes suitable for receiving a cutting tool. Plural anchoring elements are provided to attach the template to the jawbone.

In another embodiment, a system useful in a dental implant procedure includes means for scanning an implantation site on a patient's jawbone; means for simulating the implantation site; and means for determining nerve-rich areas or nerve paths in the jawbone. A production apparatus receives the simulated implantation site information and nerve-path information and produces a template suitable for locating attachment hole positions in the jawbone while the template is separated from the jawbone by at least gum tissue of the patient. The attachment hole positions in the jawbone are located so as to avoid the determined nerve paths in the jawbone.

In another aspect of this embodiment, a device includes a computer processor and necessary peripherals arranged to indicate a holed template shape for application to the bone, with the gum lying in between. The processor may be further arranged, with the aid of the information obtained from the first template, and/or user information sent to the computer equipment (in so-called interactive mode between the user and the computer appliance), and/or empirical information which can be gathered from a library, fact-containing member, etc., to execute a determination function so as to determine nerve-rich areas of the bone (jaw bone). The computer processor may be arranged to provide, in addition to data on the holed template shape, data concerning positions and extents for securing elements which are intended to extend through the gum and into and preferably through the whole bone (jaw bone), with account being taken of the routes of the nerve paths.

In another embodiment, a method of forming holes to attach a dental implant to a patient's jaw bone without surgical intervention in gum tissue of the patient to expose the jawbone includes scanning an implantation site on the patient's jawbone; simulating the implantation site; and determining nerve-rich areas or nerve paths in the jawbone. Implant hole and template attachment hole positions are planned at the implantation site on the jawbone responsive to simulated implantation site and determined nerve path information so as to avoid impingement on a nerve path. A template is produces which incorporates the planned implant hole and template attachment hole positions. The template is separated from the jawbone by at least the gum tissue. The template is attached to the jawbone with plural anchoring elements. One or more holes are cut or drilled in the jawbone through a corresponding implant hole position in the template.

BRIEF DESCRIPTION OF THE DRAWINGS

An apparatus, system, and method according to various aspects of this disclosure will be described below with reference to the attached drawings, in which:

FIG. 1 shows, in block diagram form, a computer based function for production of a holed template in connection with a patient, in which a scanning function is included and the scanning function is connected to a computer-based apparatus which-in turn is arranged to deliver information to production equipment for the template in question;

FIG. 2 shows, in horizontal view, a template applied to a jaw bone with the gum lying in between, and where securing elements for securing the template to a jaw bone are indicated;

FIG. 3 shows template, gum, and jaw bone in a vertical view;

FIG. 4 shows in perspective, obliquely from above right and from in front, the application of a template to a lower jaw bone;

FIG. 5 shows a rear view of the template and the jaw bone according to FIG. 4;

FIG. 6 shows, in perspective, the application of the template to an upper jaw; and FIG. 7 shows the template application according to FIG. 6 from above.

DETAILED DESCRIPTION OF THE PREFERRED EMBODIMENT

In FIG. 1, an implant site in the form of or on a jaw bone is indicated diagrammatically by 1. The jaw bone is shown in a vertical view 1a, and in a horizontal view 1b. In this exemplary embodiment, the implant site or the jaw bone is to be provided with a dental bridge and in this example, all the teeth in the jaw bone in question are to be replaced by a dental bridge. The implant can be scanned with a scanning function, which can be an X-ray function, or computed tomography.

Alternatively, the scanning of the implant site can be done in an alternative way by conventional scanning, e.g., by a camera, etc. The scanning function in question is indicated diagrammatically by 2, and the scanning function or the scanning equipment is arranged to generate scanning dependent signals in a conventional manner. The equipment comprises an apparatus 3 receiving the signals i1. This apparatus 3 is arranged to generate signals i1', as a function of the signals i1, and send them to a computer-based appliance, e.g., a computer processor and associated peripheral equipment, which is symbolized by 4.

The computer appliance may be conventional, and may, for example, have the form of a PC, The term computer appliance must be seen here in its widest sense, in which the computer appliance includes peripherals such as screen 4a and keyboard 4b and is arranged with conventional memory elements and software. The computer appliance can operate with conventional software which is added to or is arranged in a memory or memory devices 5, for example. The computer appliance can also include or can be connected to receive further information which can be used in connection with template production, for example, applications in the form of computer library functions and/or empirical functions. Such a connection function is indicated by 6 in FIG. 1.

The computer appliance is arranged to be able to simulate, for example, visually, the present implant situation as a function of the software. The appliance is also arranged to use the software to generate a template design which can be used for a particular implant situation. The generating of the design takes place in interaction with user 7 who, during the interaction, may use a visual computer screen 4a and a keyboard 4b, or voice control, or other known computer control techniques.

The simulation of the implant site and the suitable template produced for hole formation are transmitted in the form of digital signals i2 to a production site 8 for production of the model. The production site 8 can be arranged locally or at a remote point, and the information transfer can be done via the telecommunications and/or computer network which has been indicated by 9.

The production site 8 thus produces a template 10 which corresponds to the template simulated in the computer appliance. The template is provided with recesses or holes 12 guiding the hole-forming arrangement (drill) 11, with positions which correspond to the planned positions for the implants in the jaw bone. The template 10 is intended to be arranged on a jaw bone or equivalent 13 which is covered by gum 14. In accordance with the concept of the invention, the template is to be applied to the jaw bone 13 with the gum 14 lying in between.

The information i2 thus contains information concerning the template design. In addition, information i2 contains data on the positions and extents for securing elements which are intended to extend through the gum and into and preferably through the whole bone (jaw bone). In addition, information i2 contains data on the routes of nerve paths in connection with the bone/jaw bone.

In FIG. 2, the template 10 is applied on the gum and the jaw bone. Information on applications of the implants from the computer appliance 4 (see FIG. 1) have resulted in drill hole positions having been established on the template 10. In the illustrative embodiment according to FIG. 2, drill holes 15, 16, 17, 18 and 19 have been established. The application of the securing elements is arranged as a function of the hole and implant positions.

In a template 10 for a given dental bridge, for example, outer securing elements 20, 21 may be arranged to extend through the gum and the jaw bone at the ends 10a and 10b of the dental bridge and/or between the outermost and next to outermost fixtures in the dental bridge. The alternative or supplementary positions are indicated by broken lines 20a and 21a, respectively. Further securing elements 22, 23 extend through the gum and the bone at central parts 10c of the dental bridge. In accordance with the planning effected with the aid of the computer appliance 4 (see FIG. 1), the routes for the securing elements are arranged as a function of, or to avoid, the nerve paths which have been symbolized by 24, 25 in FIG. 2. The securing elements preferably extend through the jaw bone in its main horizontal direction. The securing elements are indicated diagrammatically in FIG. 2 and have a long and narrow or needle-shaped design.

The purpose of the securing elements is that they may be firmly anchored to the bone/jaw bone. The resiliency of the gum lying in between must not affect the position of the template when the template has been anchored to the bone/jaw bone by means of the anchoring elements. The formation of the holes in the bone/jaw bone means that the gum must be penetrated by the hole-forming equipment (see 11 in FIG. 1). The number of securing elements can vary from case to case. In an illustrative embodiment which applies, for example, to dental bridges, at least three securing elements are used. Two of the securing elements are arranged at the bridge ends and/or between the outermost and next to outermost fixtures in the dental bridge. The alternative or supplementary positions are indicated by broken lines 20*a* and 21*a* respectively, and one or more securing elements are arranged at the central parts.

In FIG. 3, the template is indicated by 10 and the bone or jaw bone by 13. The gum lying in between is indicated by 14. The template is provided with side recesses, two side recesses toward the front being shown by 26 and 27 in FIG. 3.

In FIGS. 4 and 5, a lower jaw is indicated by 28, and the main nerve path of the lower jaw (mental foramen) is indicated by 29. The surgical template is shown by 30 and its guide sleeves by 31. In accordance with the above, each securing element 32 can be inserted into a hole or a hole formation 33 which extends completely or partly through the template and the jaw bone, for example, in the horizontal direction. The elements have members 32*a* in the form of a head which determine the position of insertion.

In FIGS. 6 and 7, the upper jaw 34 is shown from below with the applied template 35 and its guide members 36 for securing elements 37 which are provided with a head 37*a*. As is known, each jaw bone 28, 34 has underlying bone, and, in accordance with various aspects of this disclosure, gum 28*a* located on the latter in the embodiment according to FIGS. 4 and 5 does not have to be opened. As regards the structure of the bone and of the gum, such structure is believed to be known.

The embodiments of this disclosure are not limited to the embodiments described above by way of example, and instead it can be modified within the scope of the attached patent claims and the inventive concept.

What is claimed is:

1. A method of planning the construction of a dental template, comprising:
    receiving information corresponding to a simulation of at least a portion of an implantation site, the simulation including information regarding the structure of a patient's jawbone and the location of nerve paths in the patient's jawbone;
    receiving information corresponding to at least one desired implant location in the patient's jawbone, the desired implant location determined at least in part using the simulation and defining an axis through the patient's jawbone;
    receiving information corresponding to at least one desired anchoring element location in the patient's jawbone, the desired anchoring element location determined at least in part using the simulation and so as to avoid the nerve paths in the patient's jawbone and so as to not intersect the axis; and
    generating, by at least one computer processor, data corresponding to a dental template design based on the simulation, based on the at least one desired implant location and based on the at least one desired anchoring element location, the desired implant location corresponding to a location in the jawbone for the planned insertion of a dental implant at the implantation site, the desired anchoring element location corresponding location in the jawbone for the planned insertion of an anchoring element that is configured to temporarily attach to the jawbone a dental template that is constructed using the dental template design.

2. The method of claim 1, further comprising constructing a dental template using the dental template design, the dental template configured to be placed over the patient's gum tissue surrounding the jawbone, the dental template comprising:
    a first wall having at least one guide hole formed therethrough corresponding to the desired implant location;
    a first sidewall having at least one anchor hole formed therethrough corresponding to the desired anchoring element location; and
    a second sidewall;
    the first wall, the first sidewall and the second sidewall together defining a channel configured to follow a contour of the gum tissue.

3. The method of claim 2, further comprising:
    placing the template over the patient's gum tissue;
    extending a cutting tool through a first anchoring hole of the at least one anchor hole of the template, through the gum tissue, and at least partially into the jawbone to form a first hole in the jawbone; and
    inserting a first anchoring element through the first anchoring hole and into the first hole in the jawbone, the first anchoring element acting to attach the template to the jawbone while avoiding the nerve paths in the jawbone and not intersecting the axis defined by the at least one guide hole.

4. The method of claim 3, wherein after insertion of the first anchoring element the resiliency of the patient's gum tissue does not affect the position of the template with respect to the jaw bone.

5. The method of claim 3, wherein a head portion of the first anchoring element defines a depth of insertion of a needle-shaped portion of the first anchoring element into the first hole in the jawbone, the head portion having a wider-cross sectional area than the needle-shaped portion.

6. The method of claim 3, wherein the inserted first anchoring element extends completely through the jawbone.

7. The method of claim 3, further comprising:
    extending a cutting tool through a second anchoring hole of the at least one anchor hole of the template, through the gum tissue, and at least partially into the jawbone to form a second hole in the jawbone; and
    inserting a second anchoring element through the second anchoring hole and into the second hole in the jawbone, the second anchoring element acting to attach the template to the jawbone while avoiding the nerve paths in the jawbone and not intersecting the axis defined by the at least one guide hole.

8. The method of claim 7, wherein after insertion of the first and second anchoring elements the resiliency of the gum tissue does not affect the position of the template with respect to the jaw bone.

9. The method of claim 1, wherein the at least one desired anchoring element location is substantially perpendicular to the at least one desired implant location.

10. The method of claim 1, wherein the dental template design defines a representation of a dental template comprising:
    a first wall having at least one guide hole formed therethrough corresponding to the desired implant location;
    a first sidewall having at least one anchor hole formed therethrough corresponding to the desired anchoring element location; and
    a second sidewall;
    the first wall, the first sidewall and the second sidewall together defining a channel configured to follow a contour of the gum tissue.

* * * * *

UNITED STATES PATENT AND TRADEMARK OFFICE
CERTIFICATE OF CORRECTION

PATENT NO. : 8,142,189 B2  
APPLICATION NO. : 12/548328  
DATED : March 27, 2012  
INVENTOR(S) : Brajnovic Page 1 of 1

It is certified that error appears in the above-identified patent and that said Letters Patent is hereby corrected as shown below:

On the Title Page, item [73], Change "Noble" to --Nobel--.

In the Specification

In column 3 at line 10, Change "computer based" to --computer-based--.

In column 3 at line 56, Change "PC," to --PC--.

In the Claims

In column 5 at line 59, In Claim 1, after "corresponding" insert --to a--.

Signed and Sealed this  
Second Day of July, 2013

Teresa Stanek Rea  
*Acting Director of the United States Patent and Trademark Office*